United States Patent [19]

Cocks et al.

[11] Patent Number: 4,825,851
[45] Date of Patent: May 2, 1989

[54] METHOD FOR COMMINUTING KIDNEY STONES

[75] Inventors: Franklin H. Cocks; Scott R. Akers, both of Durham, N.C.

[73] Assignee: Duke University, Durham, N.C.

[21] Appl. No.: 132,413

[22] Filed: Dec. 14, 1987

[51] Int. Cl.$^4$ .............................................. A61B 17/22
[52] U.S. Cl. .................................. 128/24 A; 128/328; 604/22
[58] Field of Search ................ 128/24 A, 328; 604/22

[56] References Cited

FOREIGN PATENT DOCUMENTS 0007416  1/1982  Japan ................................... 128/328
2019154  1/1987  Japan ................................... 128/328

OTHER PUBLICATIONS

Johrde et al., Fracture Strength Studies of Renal Calculi, Journal of Materials Science Letters 4 (1985) pp. 1264 & 1265.

Suby et al., Properties of Organic Acid Solutions which Determine Their Irritability to the Bladder Mucous Membrane and the Effect of Magnesium Ions in Overcoming this Irritability, pp. 549 & 550.

Johrde et al., Microhardness Studies of Renal Calculi, Materials Letters, vol. 3, No. 3, Jan. 1985, pp. 111, 112, 113 & 114.

*Primary Examiner*—Ruth S. Smith
*Attorney, Agent, or Firm*—Richard E. Jenkins

[57] ABSTRACT

A method for comminuting kidney stones including treating a stone to be comminuted with a surface energy-lowering solution and applying acoustic impulses to the stone so as to pulverize the stone into fragments small enough to be passed through the ureter and urethra.

6 Claims, No Drawings

METHOD FOR COMMINUTING KIDNEY STONES

TECHNICAL FIELD

This invention relates generally to a method for comminuting kidney stones utilizing acoustic impulses, and more specifically to a chemical treatment method which enhances the pulverizing effect of extracorporeal shock wave lithotripsy.

BACKGROUND ART

Kidney stones have always been a painful affliction to men and women of all ages. These stones, also known as renal calculi, develop within the kidney and are in many cases too large to pass through the ureter and urethra. The stones are composed of rigid crystalline components such as calcium oxalates and phosphates and are often difficult to destroy. Thus, kidney stones must either be surgically removed or somehow reduced to fragments small enough to comfortably pass through the ureter and urethra.

Various techniques have been developed in an attempt to provide a safe and effective method of eliminating kidney stones from the human body. One such technique involves the dissolution of urinary calculi by organic or inorganic acid solutions or reagents. This technique suffers from the fact that the acid solutions or reagents can be very irritating to the patient undergoing treatment.

Presently, several non-invasive sonic methods and invasive ultrasonic and laser fragmentation methods to destroy kidney stones are being explored. For example, extracorporeal shock wave lithotripsy (ESWL) is of considerable current interest and involves applying focused intense acoustic impulses which produce pressure waves greater than one kbar in amplitude. These acoustic impulses are repeatedly applied to the stone until the stone is pulverized or comminuted into fragments small enough to be passed through the ureter and urethra. Unfortunately, the acoustic pulses cannot be precisely focused onto the stone and therefore portions of the healthy kidney normally receive some of the concentrated shock waves. Since the pulses often have to be repeated up to 2000 times, the healthy portions of the kidney receiving the shock waves can be injured, resulting in hematuria. Furthermore, the shock-producing electrodes utilized in ESWL are expensive and have a limited useful life. Since ESWL requires extensive repetition of acoustic impulses, the electrodes frequently become exhausted and require replacement which results in considerable lithotripter equipment expense and inconvenience.

A need therefore exists for a method of acoustically comminuting kidney stones which utilizes a reduced number of acoustic impulses so as to minimize trauma to healthy tissue and reduce exhaustion of shock-producing electrodes in ESWL equipment. The novel technique disclosed hereinafter should overcome these deficiencies associated with current renal calculi comminution techniques.

SUMMARY OF THE INVENTION

The kidney stone comminution method of the present invention involves exposing a stone to be treated to a solution which lowers the fracture strength of the stone and then subjecting the stone to acoustic impulses so that the stone is pulverized into fragments which will safely pass through the ureter and urethra. While it is not known with certainty why particular solutions can lower the fracture strength of kidney stones, it is believed that such solutions act to reduce the surface energy of the stone. The surface energy-lowering solution may be introduced into the kidney by means of catheters normally used during lithotripter treatment. The lower fracture strength or hardness of the stone provides for fewer repetitions of pulses being required to sufficiently comminute the stone. The reduction in repetitions of pulses results in less damage to healthy kidney tissue and less exhaustion or depletion of the impulse-producing electrodes of ESWL equipment.

It is therefore a principal object of the present invention to provide a method of acoustically comminuting renal calculi which minimizes damage to healthy portions of a kidney.

It is a further object of the present invention to provide a method of acoustically pulverizing kidney stones which will avoid rapid exhaustion of the impulse-producing electrodes utilized by ESWL equipment.

It is still a further object of the present invention to provide a method of acoustically comminuting kidney stones which requires minimal repetition of impulses in order to fully pulverize the stone into fragments small enough to comfortably pass through the ureter and urethra.

BEST MODE FOR CARRYING OUT THE INVENTION

The method of the present invention involves first treating a stone to be comminuted with a surface energy-lowering solution before applying acoustic impulses to the stone to pulverize it into fragments small enough to pass through the ureter and urethra. The present method can be carried out during normal lithotripter treatment and utilizes the catheters typically associated with lithotripter treatment.

The surface energy-lowering solution is passed through a catheter into the kidney so as to come into contact with the stone to be pulverized. The solution is usually injected into the kidney prior to the application of the acoustic shocks, and the length of exposure before shock treatment can range from about 5 minutes to about 18 hours. Normally, the stones are exposed to the surface energy-lowering solution during the actual pulverization treatment.

Any lithotripter which produces acoustic shocks of sufficient strength to comminute kidney stones can be utilized in practicing the method of the present invention. However, the preferred apparatus used in conjunction with the present method is a DORNIER lithotripter operated under typical clinical voltage conditions ranging from 18 kV to 21 kV.

The method of the present invention can be used to comminute substantially any type of kidney stone. It has been discovered, however, that the present method is particularly effective in pulverizing oxalate and phosphate kidney stones. Oxalate stone herein refers to a stone containing at least 60 percent of calcium oxalate dehydrate (COD) and/or calcium oxalate monohydrate (COM). Phosphate stone herein refers to a stone containing at least 60 percent of magnesium ammonium phosphate hexahydrate (MAPH), carbonate apatite (CA) and/or hydroxy apatite (HA). The oxalate stones contemplated by the present invention may also contain small amounts of carbonate apatite or hydroxy apatite. Likewise, the phosphate stones contemplated by the present invention may contain small amounts of calcium oxalate dehydrate or calcium oxalate monohydrate.

The surface energy-lowering solution contemplated by the present invention can be any solution which will decrease the fracture strength or hardness of a stone so that it will be more susceptible to the pulverizing effect of acoustic impulses. A surface energy-lowering solution utilized in the present invention should be non-irritating to the urinary passage of the epithelium, non-toxic, and easy to make and store.

It has surprisingly been found that a citric acid solution is particularly effective for weakening phosphate stones. Citric acid solution herein refers to any surface energy-lowering solution containing citrate ions. The preferred citric acid solution for use in practicing the method of the present invention comprises from about 20 to about 40 grams of citric acid, from about 2 to about 6 grams of anhydrous magnesium oxide, from about 3 to about 7 grams of anhydrous sodium carbonate and from about 800 to about 1200 cc of distilled water. It should be understood that the active ingredient in the citric acid solution is the citric acid which releases citrate ions. The magnesium oxide is added to the solution in order to render the solution less irritating to the mucous membranes. Therefore, any solution containing the active citrate ions is contemplated by the present invention and the addition of buffers or neutralizers thereto is a matter of choice well known within the art.

It has also been found that a basified synthetic urine is particularly effective in weakening oxalate stones. Basified synthetic urine herein refers to any synthetic urine known in the art, or any variation thereof, having a pH greater than 7. The preferred synthetic urine of the present invention which is particularly effective in weakening oxalate stones comprises from about 16 to about 20 grams of urea, from about 6 to about 9 grams of sodium chloride, from about 2 to about 5 grams of potassium chloride, from about 0.5 to about 2.0 grams of creatinine, from about 0.5 to about 2.0 grams of glycine, from about 0.2 to about 0.9 grams of hippuric acid, from about 0.2 to about 0.9 grams of citric acid and from about 800 to about 1200 cc of water. The pH of the synthetic urine can be adjusted with concentrated sodium hydroxide or hydrogen chloride. It has been found that a synthetic urine having a high pH is extremely effective in weakening oxalate stones. The pH of the synthetic urine utilized in the present invention is preferably between about 7.5 and about 11.0.

CLINICAL TESTING DATA

The effectiveness of the method of the present invention was tested under clinical conditions using a DORNIER lithotripter operated under typical clinical voltage conditions ranging from 18 kV to 21 kV. Table 1 indicates the components of the synthetic urine utilized in the testing, and Table 2 indicates the specific ingredients and amounts of the citric acid solution used during testing.

For the clinical testing, each stone was severed into two equal halves with one half being used for the control environment of the synthetic urine at neutral pH 7 with the other half being used for the altered environment either consisting of synthetic urine of acidic or basic pH or of the citric acid solution. The calculi to be tested were contained in a flexible elastomeric fixture which contained both the stones and the environment to which the stones were subjected. This fixture was suspended in the water-filled lithotripter tub and positioned using the standard X-ray positioning technique for the DORNIER lithotripter. The stones were exposed to the synthetic urine solutions or the citric acid solutions prior to being subjected to acoustic shocks for an exposure time ranging from 1 hour to 18 hours. The stones were then subjected to 300 acoustic shocks and thereafter were allowed another hour of exposure to the synthetic urine or citric acid solutions. The comminuted stone fragments were washed with distilled water to remove any salts remaining from the solution to which they had been exposed and weighed after sufficient desiccation over calcium sulphate. Final drying of the comminuted stone fragments was carried out at 37 degrees C and a weight loss correction was made to account for the additional water loss at this temperature compared to drying at 25 degrees C.

The degree of comminution was quantitatively assessed by sequential sieving of the dried fragments using a series of U. S. standard sieves. The mesh dimensions of the series of sieves used is shown in Table 3. Table 4 describes the compositions (as supplied by commercial stone analysis laboratories) of the stones used in each experiment. Table 5 displays the data obtained for calculi consisting primarily of oxalate exposed to synthetic urine of various pH for 18 hours, and Table 6 displays the data obtained for calculi consisting primarily of magnesium ammonium phosphate hexahydrate and calcium apatite exposed either to synthetic urine of pH 7 or to the citric acid solution for times ranging from 1 hour to 18 hours. Table 7 displays data obtained for calculi consisting primarily of magnesium ammonium phosphate hexahydrate and calcium apatite exposed either to synthetic urine of pH 7 or to the citric acid solution for 5 minutes pre-exposure and 3 minutes post-exposure times, respectively.

TABLE 1

| Constituents | Molecular Formula | Synthetic Urine Concentration (gm./L.) |
|---|---|---|
| Urea | $H_2NCONH_2$ | 17.5 |
| Sodium Chloride | NaCl | 7.6 |
| Potassium Chloride | KCl | .3.4 |
| Creatinine | $C_4H_7N_3O$ | 1.0 |
| Glycine | $C_2H_5NO_2$ | 0.93 |
| Hippuric Acid | $HC_2H_6NO_3$ | 0.64 |
| Citric Acid | $C_6H_8O_7$ | 0.54 |
| Water | $H_2O$ | 1.0 liter/day |

TABLE 2

| Compound | WEIGHT (GRAMS) |
|---|---|
| Citric Acid (Monohydrate) | 32.5 |
| Magnesium Oxide (Anhydrous) | 3.80 |
| Sodium Carbonate (Anhydrous) | 4.40 |
| Distilled Water | 1000 cc |

TABLE 3

| | Nominal Sieve Opening | |
|---|---|---|
| Sieve No. | Inches | (mm.) |
| No. 8 | 0.187 | (2.36) |
| No. 16 | 0.0469 | (1.18) |
| No. 30 | 0.0234 | (0.600) |
| No. 50 | 0.0117 | (0.300) |
| No. 100 | 0.0059 | (0.150) |
| No. 200 | 0.0029 | (0.075) |
| No. 400 | 0.0015 | (0.038) |

TABLE 4

| Experiment Number | Stone Component: Weight Percent |
|---|---|
| 1 | COD:65/COM:25/CA:10 |
| 2 | COD:66/COM:20/HA:14 |
| 3 | COD:66/COM:20/HA:14 |
| 4 | COM:70/CA:30 |
| 5 | COM:80/COD:20 |
| 6 | COM:90/HA:10 |
| 7 | MAPH:80/CA:20 |
| 8 | MAPH:80/CA:20 |
| 9 | MAPH:100 |
| 10 | APH:60/CA:40 |
| 11 | MAPH:60/CA:40 |
| 12 | MAPH:65/CA:35 |
| 13 | MAPH:50/CA:50 |

Note:
CA = carbonate apatite, MAPH = magnesium ammonium phosphate hexahydrate, HA = hydroxy apatite, COD = calcium oxalate dihydrate, COM = calcium oxalate monohydrate.

TABLE 5

| Expt. No. | Time in Solution (hrs.) | Type of Solution | Sieve #: Stone Fraction Weight % Retained on Specified Sieves 8, 16, 30, 50 | 100, 200, 400, −400 |
|---|---|---|---|---|
| 1 | 18 | Syn. 7 | 62.2 | 37.8 |
|   | 18 | Syn. 10 | 58.2 | 41.8 |
| 2 | 18 | Syn. 3 | 41.1 | 58.9 |
|   | 18 | Syn. 11 | 33.0 | 67.0 |
| 3 | 18 | Syn. 7 | 35.4 | 64.6 |
|   | 18 | Syn. 11 | 33.3 | 66.7 |
| 4 | 18 | Syn. 7 | 69.0 | 31.0 |
|   | 18 | Syn. 11 | 61.8 | 38.2 |
| 5 | 18 | Syn. 3 | 64.9 | 35.1 |
|   | 18 | Syn. 7 | 91.7 | 8.3 |
| 6 | 18 | Syn. 3 | 88.1 | 11.9 |
|   | 18 | Syn. 7 | 62.6 | 37.4 |

TABLE 6

| Expt. No. | Time in Solution (hrs.) | Type of Solution | Sieve #: Stone Fraction Weight % Retained on Specified Seives 8, 16, 30, 50 | 100, 200, 400, −400 |
|---|---|---|---|---|
| 7 | 18 | Syn. 7 | 75.0 | 25.0 |
|   | 18 | Cit. | 36.8 | 63.2 |
| 8 | 18 | Syn. 7 | 68.6 | 31.4 |
|   | 18 | Cit. | 43.1 | 56.9 |
| 9 | 18 | Syn. 7 | 73.5 | 26.5 |
|   | 18 | Cit. | 26.9 | 73.1 |
| 10 | 4 | Syn. 7 | 74.7 | 25.3 |
|   | 4 | Cit. | 15.4 | 84.6 |
| 11 | 4 | Syn. 7 | 66.3 | 33.7 |
|   | 4 | Cit. | 22.7 | 77.3 |
| 12 | 3 | Syn. 7 | 50.0 | 50.0 |
|   | 3 | Cit. | 32.3 | 67.7 |
| 13 | 1 | Syn. 7 | 54.8 | 45.2 |
|   | 1 | Cit. | 25.6 | 74.4 |

NOTE:
Cit. = Citric Acid Solution, Syn. X = Synthetic Urine of pH X.

TABLE 7

| Expt. No. | Time in Solution (hrs.) | Type of Solution | Sieve #: Stone Fraction Weight % Retained on Specified Sieves 8, 16, 30, 50 | 100, 200, 400, −400 |
|---|---|---|---|---|
| 14 | 5(Min.) | Syn. 7 | 86.4 | 13.6 |
|   | 5(Min.) | Cit. | 74.4 | 25.6 |
| 15 | 5(Min.) | Syn. 7 | 89.6 | 10.4 |
|   | 5(Min.) | Cit. | 82.1 | 17.9 |
| 16 | 5(Min.) | Syn. 7 | 68.2 | 31.8 |
|   | 5(Min.) | Cit. | 58.7 | 41.3 |
| 17 | 5(Min.) | Syn. 7 | 83.9 | 16.1 |
|   | 5(Min.) | Cit. | 91.1 | 8.9 |

NOTE:
Cit. = Citric Acid Solution, Syn. X = Synthetic Urine of pH X.

As may be seen in experiments 1 through 6 (Table 5), in 5 of the 6 tests the higher pH condition resulted in a reduction in the relative quantity of material remaining on the sieves with the largest openings. In the remaining case, which was the only experiment involving a COM/COD stone, pH 3 resulted in a significantly reduced fragment size.

In the case of experiments 7 through 13 (Table 6) and experiments 14 through 17 (Table 7), it is evident that there is a marked reduction in the fraction of the stone which remains on the largest sieves for phosphate stones exposed to the citric acid solution. This result is particularly important because it is the larger fragments that are passed with the most difficulty.

The above data proves that the degree of comminution experienced during extracorporeal shock wave lithotripsy can be significantly enhanced by the use of a surface energy-lowering solution as contemplated by the method of the present invention. The use of a surface energy-lowering solution reduces the number of acoustic impulses needed for any given degree of pulverization, with a concomitant reduction in the collateral damage to the kidney as well as an increase in the number of patients who can be treated before the impulse-producing electrodes must be replaced. In fact, and very surprisingly, it has been found that as few as 200 acoustic impulses can produce a substantial degree of stone pulverization.

The present invention is not limited by the foregoing description but is intended to encompass various modifications within the scope and spirit of the invention described above. The scope of the invention is appropriately defined by the following claims.

What is claimed is:

1. A lithotripter method for comminuting kidney stones comprising:
   introducing a surface energy-lowering solution other than urine into a kidney through a catheter such that a stone within the kidney is exposed to said solution for at least 5 minutes; and
   applying at least 200 focused intense acoustic impulses to the stone after introduction of said solution;
   whereby the stone is comminuted into fragments small enough to be passed through the ureter and urethra with minimized risk of damage to the kidney from said acoustic impulses.

2. A method according to claim 1 wherein the surface energy-lowering solution is a citric acid solution.

3. A method according to claim 2 wherein the stone to be communicated is a phosphate stone.

4. A lithotripter method for comminuting phosphate kidney stones comprising:
   introducing a citric acid surface energy lowering solution into a kidney through a catheter such that a stone within the kidney is exposed to said citric acid solution; and
   applying at least 200 focused intense acoustic impulses which produce pressure waves greater than 1 kbar in amplitude to the stone;
   whereby the stone is comminuted into fragments small enough to be passed through the ureter and urethra.

5. A method according to claim 4 wherein the citric acid solution comprises from about 20 to about 40 grams of citric acid, from about 2 to about 6 grams of anhydrous magnesium oxide, from about 3 to about 7 grams of anhydrous sodium carbonate and from about 800 to about 1200 cc of distilled water.

6. A method according to claim 4 wherein the stone is exposed to the citric acid solution for at least 5 minutes before the acoustic impulses are applied.

* * * * *